United States Patent
Suarez

(10) Patent No.: US 10,548,759 B1
(45) Date of Patent: Feb. 4, 2020

(54) MEDICAL DEVICE FOR JOINT IMMOBILIZATION

(71) Applicant: Jose David Suarez, Miami, FL (US)

(72) Inventor: Jose David Suarez, Miami, FL (US)

(*) Notice: Subject to any disclaimer, the term of this patent is extended or adjusted under 35 U.S.C. 154(b) by 336 days.

(21) Appl. No.: 15/363,864

(22) Filed: Nov. 29, 2016

Related U.S. Application Data

(62) Division of application No. 14/683,849, filed on Apr. 10, 2015, now Pat. No. 9,549,838.

(51) Int. Cl.
*A61F 5/058* (2006.01)

(52) U.S. Cl.
CPC ........ *A61F 5/05816* (2013.01); *A61F 5/0585* (2013.01); *A61F 5/05858* (2013.01); *A61F 5/05866* (2013.01)

(58) Field of Classification Search
CPC ........ A61F 5/05816; A61F 5/012; A61F 5/01; A61F 5/0102; A61F 5/0111; A61F 5/0113; A61F 5/0118; A61F 5/0104; A61F 5/0106; A61F 5/0109
See application file for complete search history.

(56) References Cited

U.S. PATENT DOCUMENTS

| | | | | |
|---|---|---|---|---|
| 3,186,405 A | * | 6/1965 | Bailey | A61F 5/05816 602/13 |
| 4,378,009 A | * | 3/1983 | Rowley | A61F 5/012 128/DIG. 20 |
| 4,483,332 A | * | 11/1984 | Rind | A61L 15/07 602/13 |
| 5,641,322 A | * | 6/1997 | Silver | A61F 5/012 128/DIG. 20 |
| 6,730,052 B2 | | 5/2004 | Chow | |
| 2002/0077574 A1 | * | 6/2002 | Gildersleeve | A61F 5/012 602/16 |
| 2017/0079830 A1 | * | 3/2017 | Chhatrala | A61F 5/0118 |

* cited by examiner

*Primary Examiner* — Kari K Rodriquez
(74) *Attorney, Agent, or Firm* — Sanchelima & Associates, P.A.; Christian Sanchelima; Jesus Sanchelima

(57) ABSTRACT

An immobilization sleeve for helping user's heal predetermined joints. The immobilization sleeve includes two open ends at each distal end spaced apart by a plurality of inflatable, semi-rigid passages that extend in a braided, or crisscross, configuration from the base to the top of the sleeve. The sleeve is inserted onto a joint and is made of a resilient material that wraps around the joint of a user.

5 Claims, 4 Drawing Sheets

MEDICAL DEVICE FOR JOINT IMMOBILIZATION

OTHER RELATED APPLICATIONS

The present application is a divisional application relating to and claiming priority to parent application Ser. No. 14/683,849, filed on Apr. 10, 2015, by the same applicant.

BACKGROUND OF THE INVENTION

1. Field of the Invention

The present invention relates to a medical device for the immobilization of joints, more particularly, to a semi-rigid sleeve used to maintain a given joint in a substantially immobilized position to prevent further injury to a given area and accelerate healing. Such is advantageous in relieving symptoms of a plurality of joint injuries.

2. Description of the Related Art

When a person injures a joint, a key element of treatment is immobilization of the injury. In other words, the injury is secured to limit the movement of the injured body part. This prevents further tissue or muscular damage to an injured area while it heals.

Several designs for joint immobilization devices have been designed in the past. None of them, however, include a sleeve made of flexible material allowing for movement that enhances comfort while having semi-rigid resilient members that can be inflated to a sufficient rigidness to support a given joint. Optionally, the present invention can also be implemented with an actuating assembly in the form of a push-botton to inflate the device. A predetermined magnitude depending on the amount of immobilization desired by a user.

Applicant believes that a related reference corresponds to U.S. Pat. No. 6,730,052 issued to James Chow. The Chow reference discloses of an elbow brace extending from above the elbow to above the wrist. The Chow reference includes padding to enhance comfort and straps to anchor the brace using the person's neck. However, it differs from the present invention because the present invention uses a sleeve having semi-rigid resilient members configured in a braided, or crisscross, longitudinal configuration that supports to a user's joints, including elbows, knees and wrists. Also, the semi-rigid resilient members can be hollow and filled with air using an actuating assembly to enhance the support to a given joint. Additionally, the Chow reference does not teach or motivate one of ordinary skill in the art to include a resilient sleeve permitting uni-directional and bi-directional movement that increases comfort to a user. Moreover, the Chow reference does not disclose the use of a manual pump that can be used to fill the semi-rigid resilient members of the present invention with air.

Other documents describing the closest subject matter provide for a number of more or less complicated features that fail to solve the problem in an efficient and economical way. None of these patents suggest the novel features of the present invention.

SUMMARY OF THE INVENTION

It is one of the main objects of the present invention to provide a joint immobilization sleeve that supports a given joint while it is healing from an injury.

It is another object of this invention to provide such a joint immobilization sleeve that is comfortable when applying, removing, and using.

It is still another object of the present invention to provide such a joint immobilization sleeve that has a configuration of semi-rigid resilient members that allows effective support to a user's joint.

It is another object of the present invention to provide such a joint immobilization sleeve that includes an actuating assembly that can inflate the semi-rigid resilient members to provide enhanced support to a user's joints.

It is still another object of the present invention to provide such a joint immobilization sleeve that is lightweight, thereby being easy to store and transport.

It is yet another object of this invention to provide such a medical device that is inexpensive to implement and maintain while retaining its effectiveness.

It is another object of the present invention to include a manual pump to inflate the semi-rigid resilient members.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
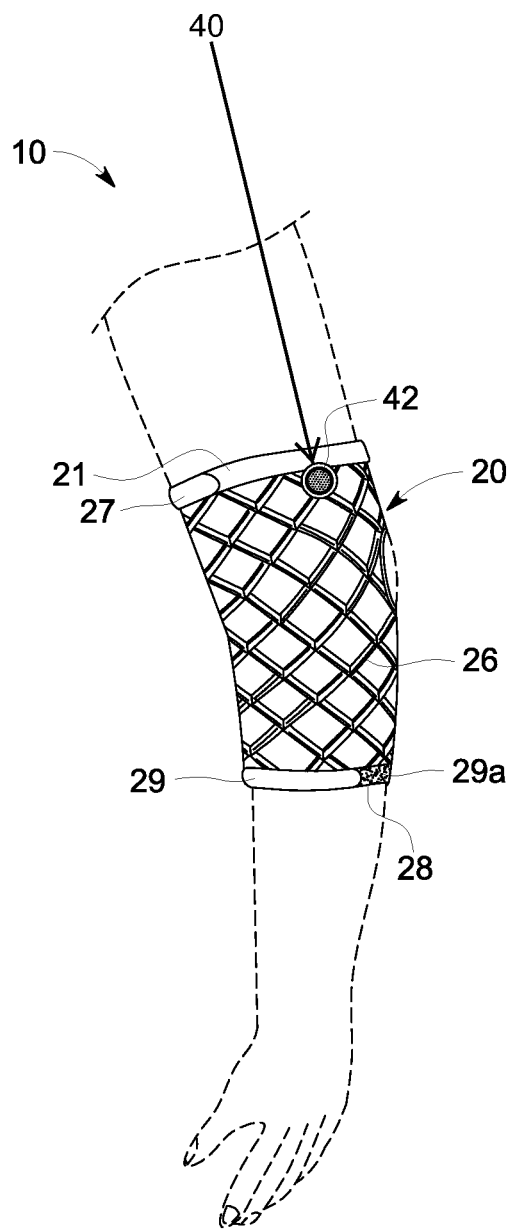
FIG. 1 shows a side view of the present invention where it has been adapted to cooperate with the elbow of a user. Hollowed resilient members 26 are inflated using pump 42 to inflate hollowed resilient members 26, thereby immobilizing a user's elbow.
Figure 1A:
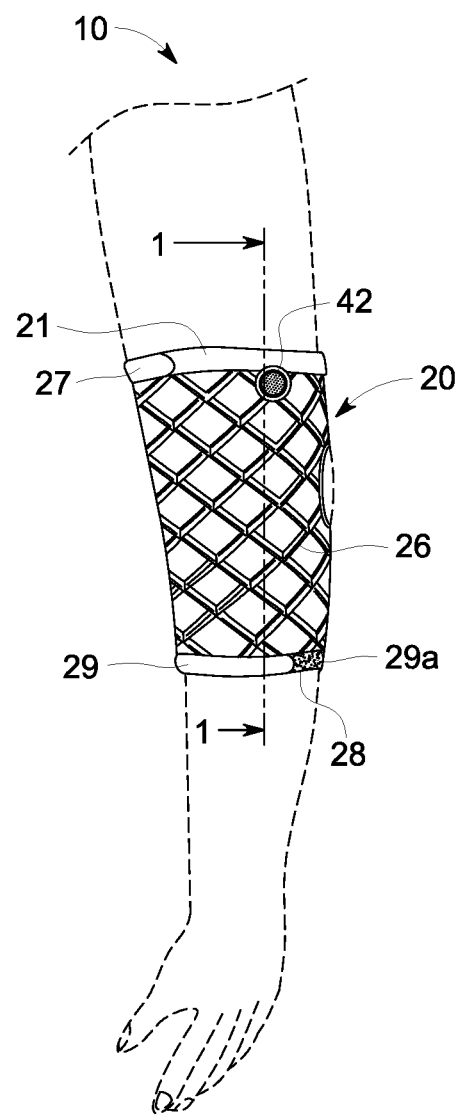
FIG. 1A is the same as FIG. 1 with the elbow of a user less bent showing the flexibility of the present invention. Also, line 1:1 is shown to reference the cross-section shown in FIG. 4.

Referring now to the drawings, where the present invention is generally referred to with numeral 10, it can be observed that it basically includes joint immobilization sleeve assembly 20. As shown in FIG. 1 joint immobilization sleeve assembly 20 includes bottom annular 28 and top annular 21 at its distal ends.

As also seen in FIG. 1, bottom annular 28 and top annular 21 are spaced apart by a plurality of hollowed resilient members 26 that extend in a braided, or crisscross, configuration from bottom annular 28 to top annular 21. Top annular member 21 includes male fastening member 27 to secure the sleeve assembly to a user's body. It can cooperate with a female fastening (member not shown). Similarly, bottom annular member 28 includes a male and female fastener member 29; 29a that secure it to a user's body at a predetermined location.

Joint immobilization sleeve assembly 20 is made of a resilient material that stretches and compresses to cooperate with the application onto a user's joint. In one embodiment, joint immobilization sleeve assembly 20 is made of a non-allergenic, thin material with a high tensile strength, such as polyethylene. Other materials such as rubber, polyurethane, latex, AT-10 resin, silicone, and neoprene can also be comfortably used with the present invention.

Hollowed resilient members 26 have a preselected flexibility and tensile strength that allows joint immobilization sleeve assembly 20 to have uni-directional and bi-directional movement. Uni-directional and bi-directional permit a user to experience forward/back and side-to-side movement, respectively. This is to enhance comfort while wearing the present invention.

Figure 2:
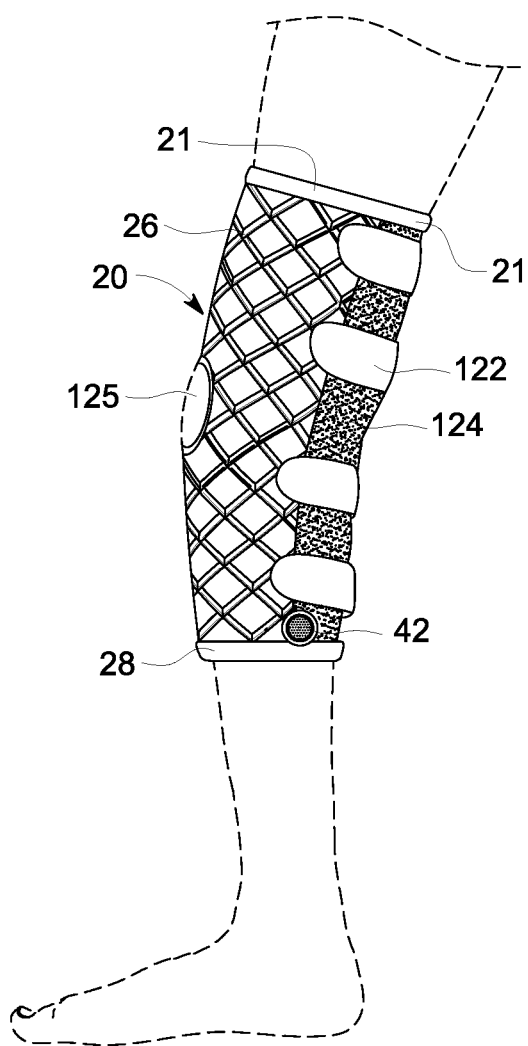
FIG. 2 shows a side view of the present invention in its operating environment where it has been adapted to cooperate with the elbow of a user. Hollowed resilient members 26 use pump 42 to inflate hollowed resilient members 26. Furthermore, male fastening members 122 cooperate with strap female portion to mount the embodiment to the leg of the user.
Figure 2A:
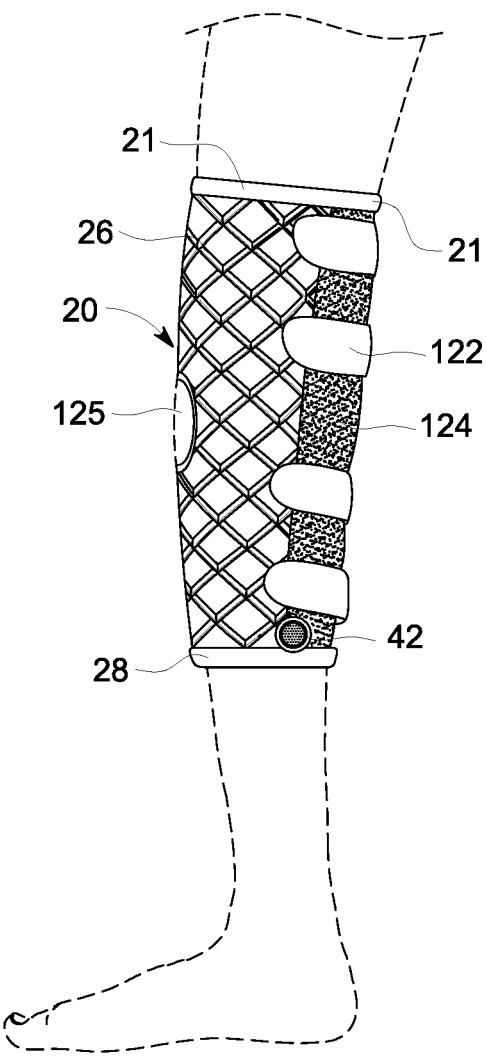
FIG. 2A is the same as FIG. 2 with the knee of a user less bent showing the flexibility of the present invention.
Figure 3:
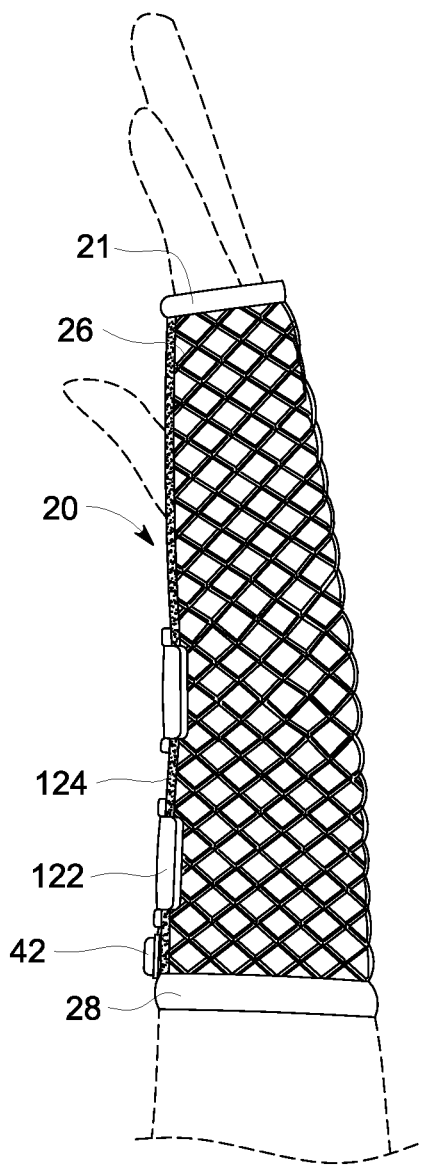
FIG. 3 shows a side view of the present invention where it has been adapted to cooperate with the wrist of a user. Hollowed resilient members 26 are used to assist in immobilizing the area and pump 42 is used to inflate hollowed resilient members 26.
Figure 3A:
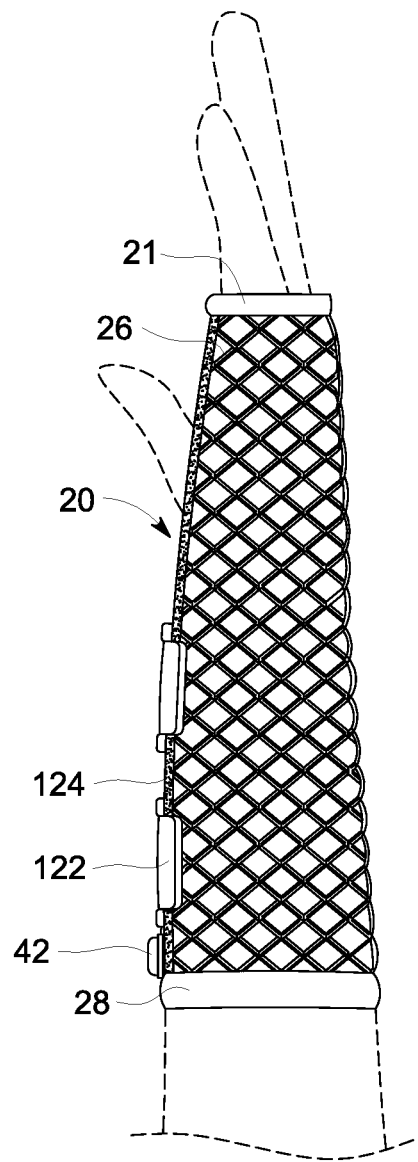
FIG. 3A is the same as FIG. 3 with the wrist of a user less bent showing the flexibility of the present invention.

In a preferred embodiment shown in FIGS. 1, 2, and 3 joint immobilization sleeve assembly 20 includes actuating assembly 40 mounted thereon.

In an alternate embodiment shown in FIGS. 2, 2A, 3, and 3A, sleeve assembly 20 can be adapted to a user's knee or wrist and includes a plurality of male fastening members 122, that cooperate with female fastening member 124. In one embodiment, male and female fastening members 122; 124 can be hook and loop fasteners.

Actuating assembly 40 includes pump 42 that a user can actuate to inflate hollowed resilient members 26 a predetermined magnitude depending on the amount of immobilization a user desires.

Pump 42 can be mounted on any of hollowed resilient members 26.

Hollowed resilient members 26 extend from bottom annular 28 in a longitudinal and braided configuration until reaching top annular 21 as seen in FIG. 1.

Figure 4:
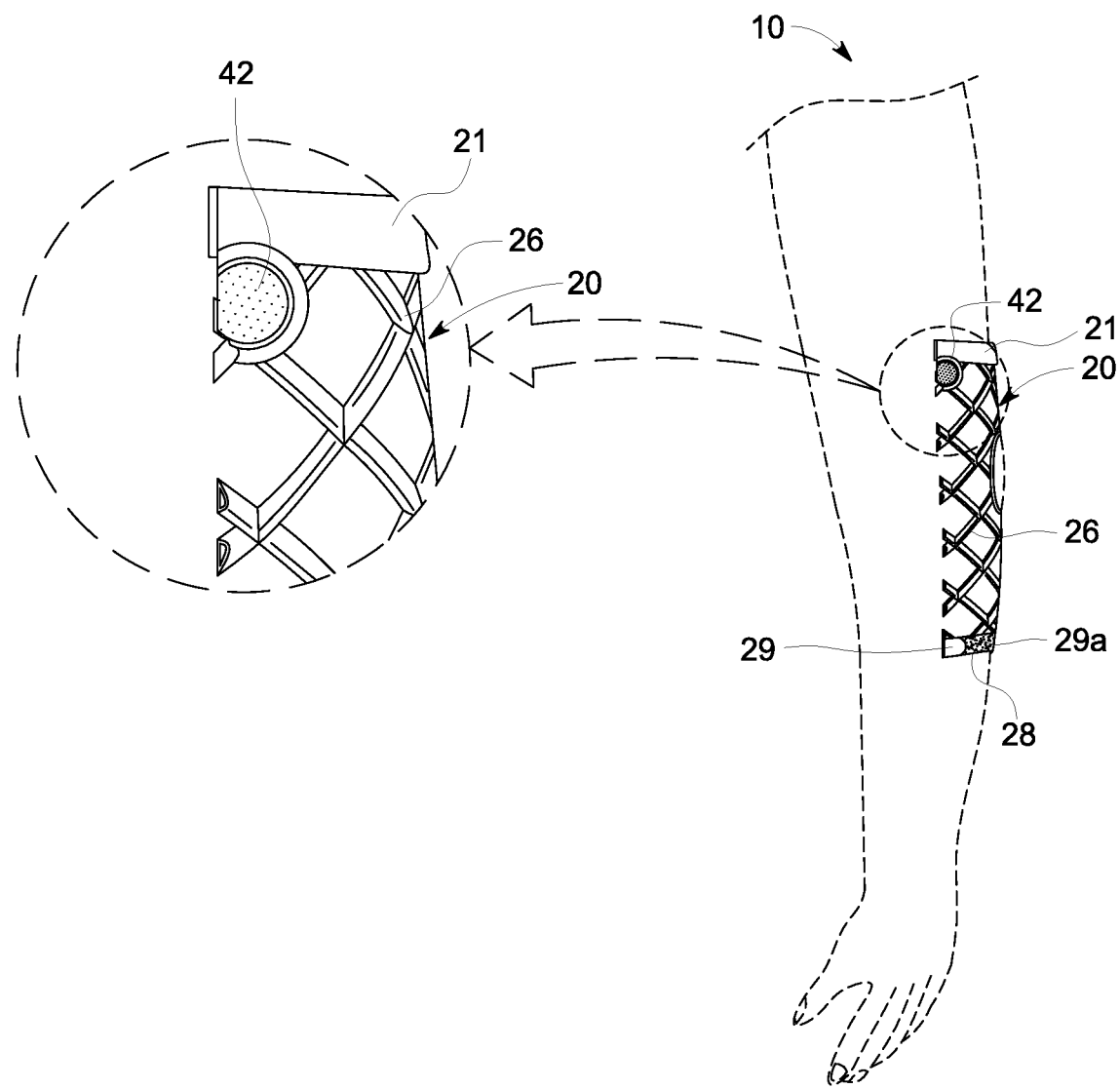
FIG. 4 shows a cross-section view of joint immobilization sleeve assembly 20. It can be the embodiment for the elbow. Hollowed resilient members 26 are hollow so they can be filled with air. This figure also shows in a cross-section, the pump 42, to understand that the pump is able to provide air to the hollowed resilient members 26 since they are connected.

Also in this alternate embodiment, when used with a knee, a kneecap opening 125 can be used to provide comfort to a user's kneecap. As shown in FIG. 4, hollowed resilient members 26 made of a material with sufficient tensile strength to maintain the joint at least partially immobilized can be seen in a cross-section view to show the openings between the inter-connected, hollowed resilient members 26.

All embodiments subject of the present invention can be covered by a solid sleeve covering to prevent fingers from being caught in between hollowed resilient members 26.

In an alternate embodiment, a valve assembly can be mounted on the hollowed resilient members 26 and cooperate with a syringe to receive air within the braided hollowed resilient member.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. An immobilization sleeve made of a resilient material that is adapted to receive a joint, said sleeve having a top circumference and a bottom circumference, said sleeve having a bottom end defined by a bottom resilient annular member and a top end defined by a top resilient annular member, said bottom resilient annular member defining said bottom circumference of said sleeve, said top resilient annular member defining said top circumference of said sleeve, said sleeve having a rear side, said sleeve having male fastening members and a female fastening member adapted to further secure said sleeve to a user's body, said female fastening member extends from said bottom resilient annular member to said top resilient annular member at said rear side of said sleeve, said male fastening members extend horizontally across said female fastening member, said male fastening members partially extend beyond said female fastening member when said male fastening members engage said female fastening member, said sleeve further including inter-connected, hollowed resilient members having an exterior surface and an interior, said top resilient annular member and said bottom resilient annular member having ring-like configurations and are each separate elements from said inter-connected, hollowed resilient members, the inter-connected, hollow resilient members include a first set of resilient members extending upwardly and diagonally starting from a left side of said sleeve to a right side of said sleeve and the inter-connected, hollow resilient members also include a second set of inter-connected, hollowed resilient members extending upwardly and diagonally starting from said right side to said left side, each of said inter-connected, hollowed resilient members in said first set being parallel to one another, each of said inter-connected, hollowed resilient members in said second set being parallel to one another, said first set and said second set are interconnected to create a braided configuration, said inter-connected, hollowed resilient members configured to allow air to flow between each other, an inflating assembly mounted to the exterior surface of said inter-connected, hollowed resilient members adjacent to said bottom end, said inflating assembly having a circumference, said inflating assembly having a bottom side that includes an opening that connects with said inter-connected, hollowed resilient members.

2. The immobilization sleeve of claim 1 having a cover unit mounted flush thereon to cover all of said hollowed resilient members.

3. The immobilization sleeve of claim 1 having a knee opening that when configured to a knee provides comfort to a user's kneecap.

4. The immobilization sleeve of claim 1, wherein said inflating assembly includes a manual pump mounted to said hollowed resilient members, said manual pump adapted to allow pumped air to enter said hollowed resilient members until a desired level of immobilization is reached.

5. The immobilization sleeve of claim 1, wherein said top resilient annular member and bottom resilient annular member are parallel to each other.

* * * * *